United States Patent [19]

Levine

[11] Patent Number: 4,559,949
[45] Date of Patent: * Dec. 24, 1985

[54] STOOL SAMPLING DEVICE

[76] Inventor: Robert A. Levine, 31 Pilgrim La., Guilford, Conn. 06437

[ * ] Notice: The portion of the term of this patent subsequent to Apr. 7, 1998 has been disclaimed.

[21] Appl. No.: 523,264

[22] Filed: Aug. 15, 1983

Related U.S. Application Data

[60] Division of Ser. No. 266,151, May 22, 1981, Pat. No. 4,420,353, which is a continuation-in-part of Ser. No. 203,083, Nov. 3, 1980, Pat. No. 4,367,750, and a continuation-in-part of Ser. No. 110,437, Jan. 7, 1980, Pat. No. 4,273,741, which is a continuation-in-part of Ser. No. 55,636, Jul. 9, 1979, Pat. No. 4,259,964.

[51] Int. Cl.[4] .................. A61B 10/00; G01N 1/02; G01N 33/52; G01N 33/72
[52] U.S. Cl. .................. 128/638; 128/155; 128/759; 422/56; 422/58; 422/61; 436/66; 604/361; 604/385 R
[58] Field of Search .............. 128/638, 759, 749, 756, 128/155; 422/56, 57, 58, 61; 436/66; 604/358, 385 R, 361

[56] References Cited

U.S. PATENT DOCUMENTS

| 3,689,224 | 9/1972 | Agnew et al. | 422/61 |
| 3,918,454 | 11/1975 | Korodi et al. | 604/361 |
| 3,965,888 | 6/1976 | Bender | 128/759 |
| 3,996,006 | 12/1976 | Pagano | 422/56 X |
| 4,055,394 | 10/1977 | Friedman et al. | 422/56 |
| 4,199,550 | 4/1980 | Wielinger et al. | 422/56 X |
| 4,225,557 | 9/1980 | Hartl et al. | 422/58 X |
| 4,259,964 | 4/1981 | Levine | 128/638 |
| 4,273,741 | 6/1981 | Levine | 422/56 |
| 4,367,750 | 1/1983 | Levine | 128/638 |

Primary Examiner—Barry S. Richman
Assistant Examiner—Robert J. Hill, Jr.
Attorney, Agent, or Firm—William W. Jones

[57] ABSTRACT

Disclosed is a device for collection of a stool sample to be used in the clinical evaluation of a patient for gastrointestinal bleeding. This device comprises a multilayered composite, which can be used in a manner analogous to toilet tissue, to obtain a stool sample which can thereafter be evaluated for occult blood.

4 Claims, 7 Drawing Figures

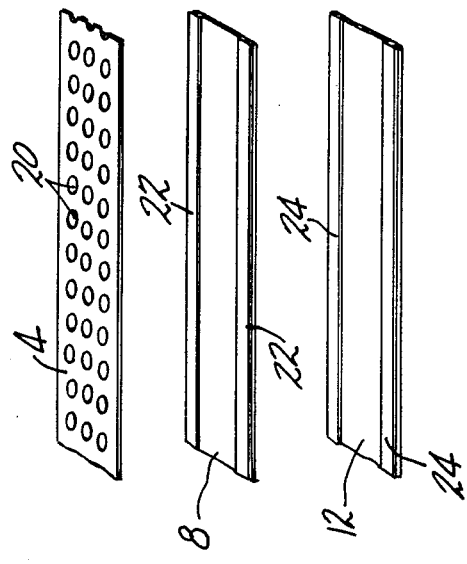
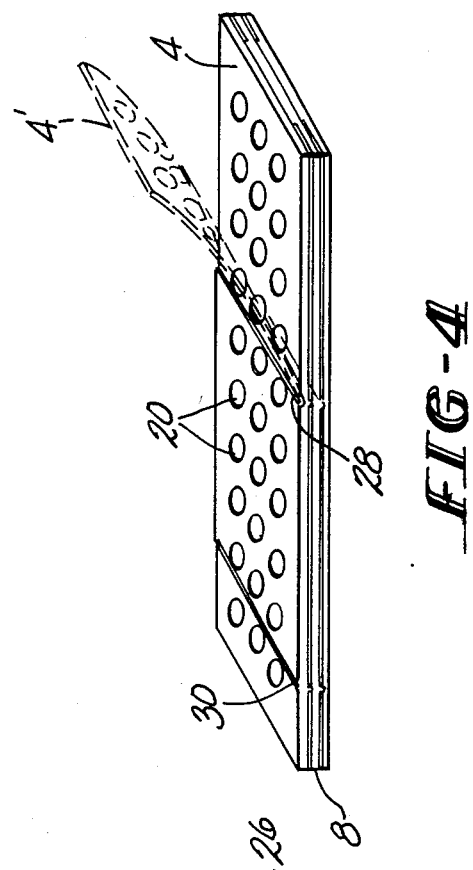
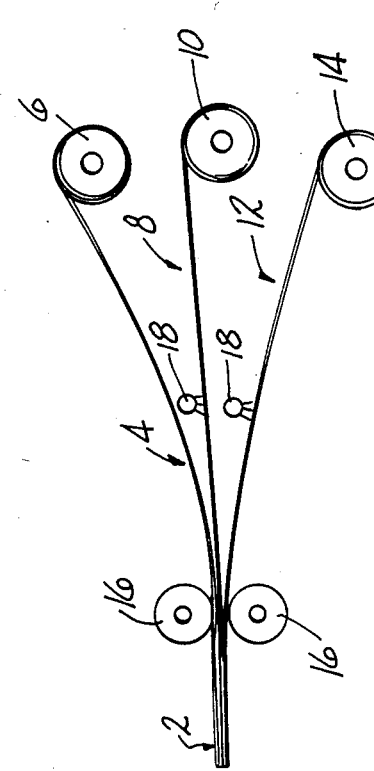
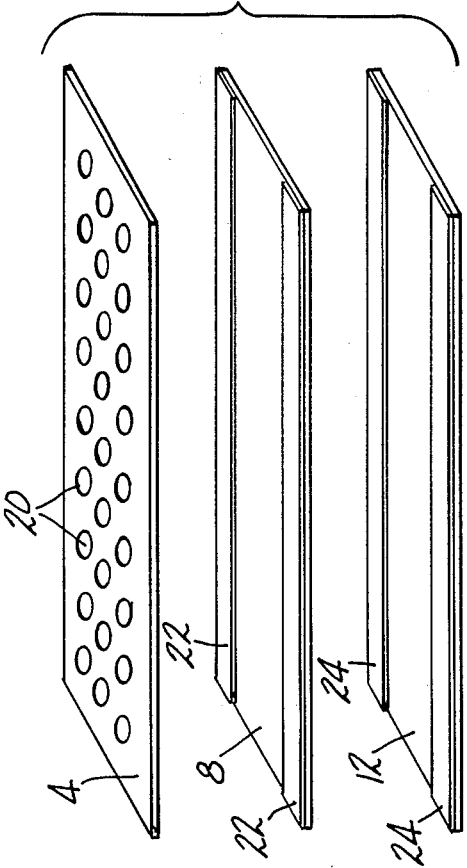

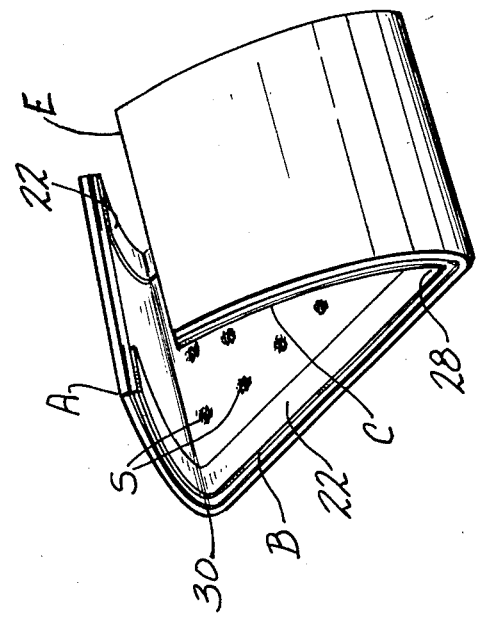
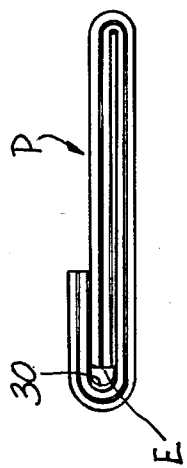
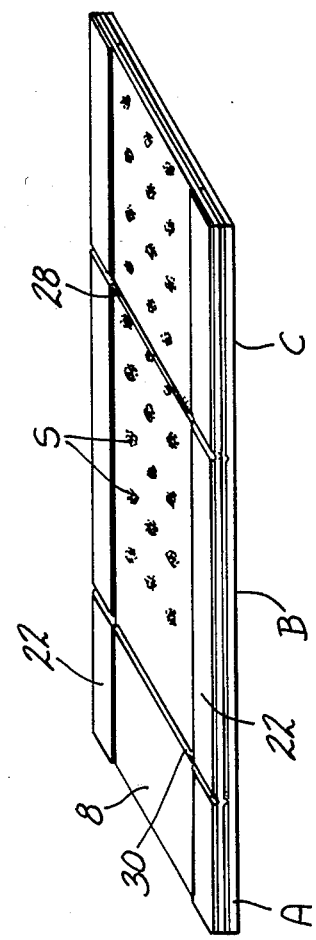

STOOL SAMPLING DEVICE

CROSS REFERENCE TO RELATED APPLICATIONS

This application is a divisional of co-pending U.S. application Ser. No. 266,151 (filed May 22, 1981)—now U.S. Pat. No. 4,420,353; which in turn is a continuation-in-part of co-pending U.S. application Ser. No. 203,083 (filed Nov. 3, 1980)—now U.S. Pat. No. 4,367,750 and U.S. application Ser. No. 110,437 (filed Jan. 7, 1980)—now U.S. Pat. No. 4,273,741; which in turn is a continuation-in-part of co-pending U.S. application Ser. No. 055,636 (filed July 9, 1979)—now U.S. Pat. No. 4,259,964.

BACKGROUND OF THE INVENTION

A procedure which is routinely performed in physicians' offices in connection with physical examinations involves the testing of the patient's stool for the presence of occult blood. The physician typically will obtain a sample of the patient's stool by probing the patient's rectum with a rubber glove. The sample which is thus obtained is typically tested with guaiac and hydrogen peroxide reagents, which, in the presence of occult blood in the stool sample, will produce a characteristic blue coloration on the paper onto which the stool is smeared.

The obvious discomfort attendant to this type of stool sample gathering has produced a number of alternatives in the prior art. These alternatives involve paraphernalia which the patient takes home from the physician's office, and which the patient uses in the privacy of his home to obtain the stool sample, which is then transmitted back to the physician's office for the testing. This paraphernalia will include a specimen holder of some type, and a device, usually a wooden stick, for obtaining a stool sample after defecation. The sample is obtained from the toilet after defecation and transferred to the specimen holder, which is then returned to the physician's office. The stick is discarded after the stool sample is obtained. U.S. Pat. No. 3,996,006, issued Dec. 7, 1976; U.S. Pat. No. 4,092,120, issued May 30, 1978; and U.S. Pat. No. 4,199,550, issued Apr. 22, 1980 are illustrative of such prior art stool sampling devices.

SUMMARY OF THE INVENTION

In accordance with the present invention, there is provided a sampling device for obtaining biological samples which is formed from a first sheet means of pliant impermeable material which has a sample receiving portion on one side thereof. A second sheet means of pliant material for collecting a sample by wiping the second sheet means over a sample overlies the sample receiving portion, and the second sheet means includes at least one opening which overlies the sample receiving portion whereby the second sheet may be wiped over a sample to deliver sample onto the sample receiving portion through the at least one opening. The first sheet includes at least one fold line for folding a first portion of the one side of the first sheet over a second portion of the one side of the first sheet, with the fold line being positioned to maintain any sample on the sample receiving portion between the first and second portions. Thus, the sample on the sample receiving portion is maintained or packaged between the folded portions of the first sheet for subsequent testing.

BRIEF DESCRIPTION OF THE DRAWINGS

The invention will be further described with reference to the accompanying drawings, in which:

FIG. 1 is a schematic representation of a manufacturing assembly suitable for forming, from continuous strip components, continuous strip stock suitable for cutting for forming the stool sampling devices of this invention;

FIG. 2 is an exploded view of fragments of the several strip components of the strip stock material from which the stool sampling device of this invention is formed;

FIG. 3 is an exploded view of the several components of a stool testing device formed in accordance with an embodiment of this invention, after the device has been cut from the stock strips;

FIG. 4 is a perspective view of an embodiment of a stool testing device of this invention, showing in phantom the mode of removal of the screening layer after the stool sample has been obtained, FIG. 5 is a perspective view of an embodiment of the device of this invention after the screening layer has been removed, FIG. 6 is a side view of the stool sampling device of this invention after it has been folded into a pouch, FIG. 7 is a perspective view of a device of this invention which has been sealed, thereby isolating the sample and bacterial matter within a sealed pouch.

DETAILED DESCRIPTION OF THE INVENTION

Referring now to the drawings, there is disclosed in FIG. 1 a somewhat schematic representation of the manner in which the stock laminate used to form an embodiment of a sampling device of this invention is produced. The stock laminate is formed as a continuous strip which is cut to size after lamination. The strip laminate 2 is formed by feeding a strip 4 of the screening material layer from a roll 6 thereof, a strip 8 of the absorbent material from a roll 10 thereof, and a strip 12 of a transparent impermeable plastic material from a roll 14 thereof, through a pair of opposed pressure rolls 16. Adhesive applicating devices 18 are used to apply adhesive to the transparent impermeable plastic strip 12 and to the absorbent material strip 8 to provide a bond for the laminate 2. The adhesive applicating devices can take the form of brushes, rollers, sprays, or double-sided adhesive tape strips fed from rolls.

As will be noted from FIG. 2, the screening layer 4 is formed with a plurality of openings 20 extending in columns of rows along the mid-axial portion of the layer 4. The openings 20 serve to volumetrically control the amount of stool deposited on the absorbent layer 8 when the device is used. The adhesive disposed on the absorbent layer 8 preferably takes the form of a pair of parallel strips 22 which extend along the side edge portions of the layer 8 so that the mid portion of the layer 8 is free of adhesive. Likewise, the transparent, impermeable plastic layer 12 preferably includes parallel strips 24 of adhesive which extend along the side edge portions of the layer 12 so that the mid portion of the layer 12 is free of adhesive. The adhesive strips 22 and 24 are preferably releasable, as will be discussed hereinafter.

Once the laminate 2 has been formed, after passing through the rolls 16, the laminate 2 is cut transversely into indivdual stool sampling devices 26, as shown in FIG. 3. It will be noted that the openings 20 extend through the entire axial extent of the screening layer 4 so that stool will be deposited on the absorbent layer 8 no matter where along the device the rectum is wiped. The layer 12 is impermeable so as to retain bacteria in the stool, and is transparent so that the chemical reaction can be viewed through the layer 12. The adhesive strips 24 are preferably restricted to the sides of the strip 12 so that the coloration will be clearly visible through the layer 12 without interference from adhesive.

Once the device has been laminated and cut to size, a pair of transverse fold lines 28 and 30 formed in the device. These fold lines should preferably be formed as sharply as possible so as to aid in forming a closed pouch which will contain the stool sample for transmittal to the physician's office as tightly as possible, so that the possibility of bacterial escape from the stool sample is minimized. As noted in FIG. 4, after the device is used, the releasable adhesive strips 22 allow the screening layer 4 to be peeled off the laminate, as indicated by 4′, and discarded in the toilet by the user. It will be appreciated that the screening layer 4 acts, by means of the openings 20, to control the amount of stool which is deposited on the absorbent layer 8.

Referring to FIG. 5, it will be noted that, after the device has been used, and the screening layer 4 has been removed, there are a plurality of volumetric stool smears S deposited on the absorbent layer 8. The diameter of the openings 20, and the thickness of the screening layer 4 combine to control the volume of the stool smears S. When the screening layer 4 has been removed, the adhesive strips 22 are exposed so that the fold lines 28 and 30 can be used to form the pouch, as shown in FIGS. 6 and 7.

To form the pouch, the layers 8 and 12 are folded along the fold lines 28 and 30, as shown in FIG. 6, until the closed pouch P is formed, as shown in FIG. 7. It will be understood that the adhesive strips 22 hold the folded laminate together to keep the pouch P closed. At the same time the edge E of the laminate is spaced apart from the fold line 28 a predetermined distance so that, when the pouch P is formed, the edge E is tightly juxtaposed with the fold line 30 so that the stool smears S are contained within a relatively tightly closed pouch P thereby minimizing the possibility of escape of bacteria and odor from the interior of the pouch.

If the absorbent layer 8 is pre-impregnated with guaiac reagent, it will be appreciated that the screening layer 4 and its openings 20 will not allow the guaiac to substantially penetrate the screening layer 4 prior to or during use of the device, thus possible adverse effects of the guaiac on the patient are virtually eliminated. Of course, the device may be produced with a non-guaiac-impregnated absorbent layer; however, if the guaiac-impregnated layer is used, then the hydrogen peroxide is the only reagent which need be applied in the physician's office to perform the test. When the pouch containing the stool sample is received in the physician's office, the adhesive strips 22 can be disrupted so that the technician can peel open the pouch to apply the necessary reagents. The adhesive used is one which provides for resealability after the reagents are applied to the stool sample.

Preferably, the impermeable layer 12 will be made of transparent plastic material so that, once the necessary reagents are applied to the stool spots S, the pouch may be reclosed and the presence or absence of the characteristic blue color may be observed through the impermeable layer 12.

As previously noted, the adhesive strips 24 can be formed from a releasable adhesive so that the absorbent layer 8 can be peeled off the impermeable layer 12. The separated absorbent layer 8 bearing the stool spots S can then be used in chromatographic testing of the stool specimen.

As should be apparent, the device may be simply used by wiping the screening layer 4 of the device over the anal area after bowel movement to apply a stool sample to layer 8 for subsequent testing.

The patient will be instructed to use the device in such a manner that the stool smear will extend from section B toward section C of the device, and so that no stool will be deposited on section A. In forming the pouch P, section C will be folded first to entrap all of the stool on the device within the confines of juxtaposed sections B and C. The stool-free section A will then be folded down over sections B and C to form the outer, uncontaminated closure for the pouch P.

After the test has been performed, the closed pouch may be discarded with minimal chance of bacterial pollution from the enclosed stool sample.

It will be readily appreciated that the stool sampling device of this invention can be economically manufactured from stock endless strip components, cut to size, and scored for folding. The use of the device is simple, natural and convenient for a patient, and the device may be readily folded, after use, into a closed pouch which can be easily reopened for application of reagents, and then refolded into a closed pouch once again. The device of this invention may also be used to collect other biological samples and contain them in a similar manner.

Since many changes and variations of the disclosed embodiment of the invention may be made without departing from the inventive concept, it is not intended to limit the invention otherwise than is required by the appended claims.

What is claimed is:

1. A stool sampling device, comprising:
    a first sheet of pliant, impermeable material; an absorbent layer impregnated with a reagent for reacting with any occult blood in a fecal sample, adhesively secured to one side of said first sheet, for receiving a fecal sample;
    a second sheet of pliant material adhesively secured in overlying relationship to said absorbent layer and releasable therefrom, said second sheet having a plurality of openings coincident with at least a portion of said absorbent layer for controlling an amount of stool sample which is deposited upon said absorbent layer when said second sheet is wiped over a fecal sample;
    said first sheet being provided with at least one fold means so as to aid in forming a closed pouch to effectively isolate a stool sample within said pouch subsequent to removal of said second sheet of pliant material from the device.

2. The device of claim 1 further comprising securement means for maintaining the device in a folded condition to form a closed pouch.

3. The device of claim 1 wherein the reagent is guaiac reagent.

4. A method of collecting a stool smear comprising:
    wiping the second sheet of the sampling device of claim 1 over an anal area after a bowel movement to deliver a stool sample onto the absorbent layer.

* * * * *